United States Patent [19]
Kraus et al.

[11] Patent Number: 5,962,713
[45] Date of Patent: *Oct. 5, 1999

[54] CARBOSILANE DENDRIMERS COMPRISING SI-O-METAL BONDS, A METHOD OF PREPARING THEM AND THEIR USE

[75] Inventors: Harald Kraus; Michael Mager, both of Leverkusen, Germany

[73] Assignee: Bayer AG, Leverkusen, Germany

[ * ] Notice: This patent is subject to a terminal disclaimer.

[21] Appl. No.: 08/907,304

[22] Filed: Aug. 6, 1997

[30] Foreign Application Priority Data

Aug. 14, 1996 [DE] Germany ............... 196 32 700

[51] Int. Cl.$^6$ .................. C07F 7/08; C07F 7/28
[52] U.S. Cl. ................. 556/10; 556/9; 556/431; 556/435; 556/402; 556/404; 528/15; 528/19; 528/21
[58] Field of Search .................. 556/9, 10, 431, 556/435, 402, 404; 528/15, 19, 21

[56] References Cited

U.S. PATENT DOCUMENTS

| | | | |
|---|---|---|---|
| 5,276,110 | 1/1994 | Zhou et al. | 525/479 |
| 5,548,051 | 8/1996 | Michalczyk et al. | 556/431 X |
| 5,677,410 | 10/1997 | Mager et al. | 528/15 |
| 5,679,755 | 10/1997 | Mager et al. | 556/431 X |

FOREIGN PATENT DOCUMENTS 196 03 241   7/1997   Germany .

OTHER PUBLICATIONS

Orbit Abstract of DE 196 03 241 (Jul. 10, 1997).
Abstract of DE 196 03 242 (Jan. 30, 1996).

*Primary Examiner*—Paul F. Shaver
*Attorney, Agent, or Firm*—Connolly & Hutz

[57] ABSTRACT

The present invention relates to new carbosilane dendrimers comprising Si—O-metal bonds, to a method of preparing them and to their use.

15 Claims, No Drawings

CARBOSILANE DENDRIMERS COMPRISING SI-O-METAL BONDS, A METHOD OF PREPARING THEM AND THEIR USE

The present invention relates to new carbosilane dendrimers comprising Si—O-metal bonds, to a method of preparing them and to their use.

Substances which are described as dendrimers are strongly branched molecules comprising a highly-ordered, mostly three-dimensional structure, the molecular weight of which falls within the range of that of oligomers or polymers.

However, dendrimers have the advantage that they can be deliberately synthesised with a highly uniform molecular weight, whereas customary polymers always exhibit a certain molecular weight distribution. Moreover, defined functional dendrimers can be produced, such as those containing terminal vinyl groups for example, which comprise a defined number of such reactive groups.

Hitherto, it has been possible to prepare only a very few representatives of metal-functionalised carbosilane dendrimers which differ as regards the type of bonding of the metal atoms. Carbosilane dendrimers are known, for example, to which diaminoarylnickel(II) complex fragments are bonded via Si—O—C bridges (Nature 1994, 372, 659–663), to which chromium tricarbonyl fragments are bonded to Si-phenyl groups via $\eta^6$ coordinations (J. Organomet. Chem. 1996, 509, 109–113), or to which dicobalt hexacarbonyl fragments are bonded via terminal acetylene-Si groups (Organometallics 1995, 14, 5362–5366). These compounds are of interest for catalytic processes.

Heterogenous catalysts based on doped silicates or on silicate supports are frequently used in industry. Thus aluminosilicate zeolites are used in petrochemical technology for cracking and isomerisation reactions, and titanium silicates are used for oxidation reactions, for example. Many metal complexes are also used as heterogeneous catalysts after bonding to $SiO_2$ support materials. The capacity of the metals to form Si—O-metal bonds is utilised here.

Compared with silicate materials, metal-functionalised carbosilane dendrimers are distinguished by a well-defined molecular structure and by their optimum surface/volume ratio. A further advantage is that all the metal centres on the surface of dendrimers are freely accessible. Moreover, they can be used both as homogeneous and as heterogeneous catalysts.

There is therefore a great need to provide carbosilane dendrimers comprising Si—O-metal bonds for the immobilisation and support of catalytically active substances or for the production of inorganic-organic hybrid materials.

The carbosilane dendrimers which have been known hitherto are synthesised from an initiator core by alternate hydrosilylation and Grignard reactions (e.g. U.S. Pat. No. 5,276,110; Adv. Mater. 1993, 5, 466–468; Macromolecules 1993, 26, 963–968; J. Chem. Soc., Chem. Commun. 1994, 2575–2576; Organometallics 1994, 13, 2682–2690 and DE-P 19603242.3). For example, the initiator molecule tetravinylsilane is reacted with $HSiCl_2CH_3$ in THF using a Pt catalyst. A vinylsilane which is available afresh for hydrosilylation is synthesised again by reaction with a vinylmagnesium halide. In an analogous manner, cyclic organosiloxanes can also be used as initiator nuclei; see DE-P 19603241.5. Carbosilane dendrimers are suitable, for example, for the production of hybrid materials for coatings, or as calibration substances due to their defined molecular structure.

It is known from WO 94/06807 that organic-inorganic hybrid materials can be prepared by the reaction of trialkylsiloxane-functionalised carbosilanes with metal alkoxides, water and a catalyst. Disiloxane and/or heterosiloxane bridges are produced as a result of hydrolysis and condensation processes, and a three-dimensional, glass-like network with a polymeric structure is formed.

It has now been found that metal compounds can be bonded to carbosilane dendrimers via Si—O-metal bonds (heterosiloxane bridges) and that the compounds which are thereby produced can be isolated as well-defined molecular compounds.

The present invention therefore relates to carbosilane dendrimers comprising Si—O-metal bonds, of general formula

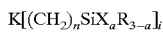

where n=2–6, preferably n=2, and R=$C_1$–$C_{18}$ alkyl and/or $C_6$–$C_{18}$ aryl, wherein n and also R can be the same or different, preferably the same, within the molecule, and wherein the other symbols and subscripts have the following meanings:

A) $K=[R_{4-i}Si]$ where i=3, 4, preferably 4 or

B) K =

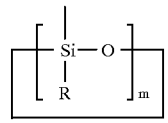

where i=m and m=3–6, preferably m=3, 4, in combination with

X=—OM when a=1, or $X=[(CH_2)_nSi(OM)R_2]$, $[(CH_2)_nSiR_{3-a}[(CH_2)_nSi(OM)R_2]_a]$ and/or $[(CH_2)_nSiR_{3-a}[(CH_2)_nSiR_{3-a}[(CH_2)_nSi(OM)R_2]_a]_a]$ when a=1–3, preferably a=3, where M is a metalloid and/or metal which may optionally contain further substituents.

The alkyl radicals R in the sense of the present invention are preferably linear or branched $C_1$–$C_5$ alkyl radicals which are optionally substituted. The term "substituted" comprises all common substituents, such as halogen, alkyl, amine, etc.

The aryl radicals R in the sense of the invention are preferably $C_6$ rings which are optionally substituted.

In one preferred form of the present invention, the carbosilane dendrimers can be described by the following formulae:

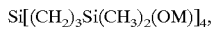

and/or

Carbosilane dendrimers of formula

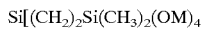

are particularly preferred.

B, Al, Ga, In, Ge, Sn, Pb, As, Sb, Bi, Ti, Zr, Hf, V, Nb, Ta, Cr, Mo, W, Re, Fe, Ru, Os, Rh, Ir, Pt, Cu, Ag and/or Au are particularly suitable as metalloids and/or metals in the sense of the invention.

The metals and/or metalloids M may contain one or more further substituents which are customary for metals and/or metalloids, for example linear, branched or cyclic alkyl, cyclopentadienyl, aryl or P-containing radicals which are optionally substituted, e.g. phosphanes such as triaryl or trialkylphosphanes; N-containing radicals, such as ethylenediamine for example; O-containing radicals, such as acetylacetonate or alcoholates, for example; or a halogen, e.g. chloride, etc.

In addition, the metals and/or metalloids can each form O bridges to one or more Si atoms, in the latter case intramolecularly, of the dendrimer molecule, preferably to one Si atom.

The preferred metals and/or metalloids in the sense of the invention are the elements Ti, Zr, Hf, V, Nb, Ta, Cr, Mo and W, Ti, Zr and Hf are particularly preferred, and Ti is most particularly preferred.

In a preferred embodiment of the present invention, the carbosilane dendrimer comprising Si—O-metal bonds is $Si[(CH_2)_2Si(CH_3)_2(OTiCp_2Cl)]_4$, which exhibits great stability (Cp=cyclopentadienyl). The bonded metal compound here is the metallocene compound $Cp_2TiCl_2$, which can be used, for example, in combination with organic aluminium compounds as a catalyst in the polymerisation of olefines (Ziegler Catalysts, Ullmann's Encyclopedia of Industrial: Chemistry, 5th Edition (1996), Vol A 28, pages 506–508). It also acts as a catalyst for epoxidation reactions of olefines, wherein the activity can be increased by employing the catalyst as a heterogenous catalyst on a $SiO_2$ base (Tetrahedron 51, No. 13, 3787–3792 (1995)).

The present invention also relates to a method of preparing the carbosilane dendrimers comprising Si—O-metal bonds according to the invention, in which an SiOH-functional carbosilane of general formula

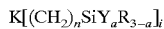

where n=2–6, preferably n =2, and R =$C_1$–$C_{18}$ alkyl and/or $C_6$–$C_{18}$aryl, wherein n and also R can be the same or different, preferably the same, within the molecule, and where A) K=[$R_{4-i}$Si]

where i 3, 4, preferably 4 or

B) K =

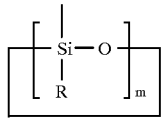

where i=m and m=3–6, preferably m=3, 4, in combination with:

Y=(OH) when a=1,

Y=[$(CH_2)_nSi(OH)R_2$], [$(CH_2)_nSiR_{3-a}[(CH_2)_nSi(OH)R_2]_a$] and/or [$(CH_2)_nSiR_{3-a}[(CH_2)_nSiR_{3-a}[(CH_2)_nSi(OH)R_2]_a]_a$] when a=1–3, preferably a =3, is reacted with at least one metal and/or metalloid compound, optionally in the presence of a base and a solvent.

In a preferred form of the invention, the SiOH-functional carbosilane dendrimers used are those of formulae

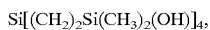

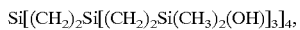

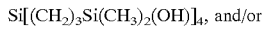

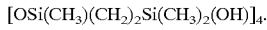

The use of $Si[(CH_2)_2Si(CH_3)_2(OH)]_4$ is particularly preferred.

The SiOH-functional carbosilane dendrimers are preferably prepared by the method described in DE-P 19603242.3 and DE-P 19603241.5.

The metal and/or metalloid compounds in the sense of the invention are characterised in that they are preferably substituted with at least one ligand Z, where Z=Cl, Br, I, OR (R=alkyl or aryl) and Si—O-metal bonds are formed with the separation of HZ. In addition, they may optionally comprise one or more substituents which are customary for metals and/or metalloids, for example linear, branched or cyclic alkyl, cyclopentadienyl, aryl radicals or P-containing radicals which are optionally substituted, e.g. phosphanes such as triaryl or trialkyl-phosphanes; N-containing radicals, such as ethylenediamine for example; O-containing radicals, such as acetylacetonate for example; or a halogen, e.g. chloride, etc. Phosphane, metal carbonyl, metal nitrosyl., metallocene, olefine and alkyne complex compounds are preferred. Metallocene compounds are particularly preferred; $Cp_2TiCl_2$ is quite particularly preferred.

Triorganoamines are preferably used as bases in the sense of the invention, wherein the organo radicals comprise all common $C_1$–$C_{18}$ alkyl, $C_6$–$C_{18}$ aryl and phenyl radicals, which may be linear or branched and may optionally be substituted, preferably trialkylamines. The alkyl most preferably corresponds to a $C_1$–$C_3$ radical. The bases are used stoichiometrically or in excess.

The method according to the invention is preferably conducted in a solvent. All common organic solvents are suitable as solvents, e.g. ether solvents such as THF, diethyl ether and tert -butyl methyl ether for example, alcohols such as methanol, ethanol and isopropanol for example, ketones such as acetone and methyl ethyl ketone for example, acetonitrile and/or dimethylsulphoxide.

The method according to the invention is conducted at temperatures from −78° C. up to the boiling point of the corresponding solvent, preferably from −20° C. up to the boiling point of the corresponding solvent, most preferably from 0° C. up to the boiling point of the corresponding solvent.

The method is preferably carried out as a homogeneous reaction, i.e. in a solvent in which both the SiOH-functional carbosilane dendrimer and the metal and/or metalloid compound dissolve without decomposition.

The present invention further relates to the use of the carbosilane dendrimers comprising Si—O-metal bonds as homogeneous or heterogeneous catalysts or as an additive or constituent for the production or functionalisation of inorganic-organic hybrid materials, e.g. for coating.

EXAMPLES OF IMPLEMENTATION

Preliminary remarks:

Synthesis was effected by means of the Schlenk technique under argon or in vacuum. TBF and triethylamine were dried by the usual laboratory methods before use and were distilled under argon. $Cp_2TiCl_2$ (obtainable commercially) was purified by sublimation.

Si[(CH₂)₂Si(CH₃)₂(OH)]₄ was prepared according to DE-P 19603242.3.

EXAMPLE

Synthesis of Si[(CH₂)₂Si(CH₃)₂(OTiCp₂Cl)]₄

A solution of 5 g Si[(CH₂)₂Si(CH₃)₂(OH)]₄ (11.34 mmole) in 150 ml THF was added drop-wise at room temperature to a solution of 11.35 g Cp₂TiCl₂ (45.6 mmole) in 500 ml THF. Thereafter, the mixture was stirred for 30 minutes at room temperature and a solution of 5.55 g NEt₃ (54.9 mmole) in 25 ml THF was added drop-wise. The batch was stirred for a further 20 hours at room temperature, whereupon a change in colour of the reaction solution from dark red to light orange was observed and a white precipitate of NEt₃*HCl was formed.

The salt formed was filtered off and all the volatile components were removed by condensation under vacuum. The product was obtained as an orange-coloured powder ¹H-NMR (d₈-THF):δ=0.08 pm (s, 6H, SiCH₃); 0.58 ppm (m, 4H, SiCH₂); 6.29 ppm (s, 10OH, TiC₅H₅).

IR (KBr trituration), band positions in cm⁻¹: 300 vw, 370 m, 390 sh, 460 w, 600 w, 670 sh, 720 sh, 760 s, 810 vs, 840 sh, 950 vs, 1020 m, 1060 w, 1120 m, 1170 vw, 1250 s, 1360 w, 1400 m, 1440 m, 2900 m, 2950 m, 3100 w.

What is claimed is:

1. Carbosilane dendrimers comprising Si—O-metal bonds, of general formula

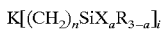

where n=2, 3, 4, 5 or 6 and R=C₁–C₁₈ alkyl or C₆–C₁₈ aryl, wherein n and also R can be the same or different within the molecule, and wherein the other symbols and subscripts have the following meanings:
A) K=[R₄₋ᵢSi]
   where i=3 or 4, or

B) K =

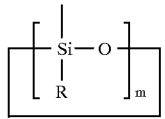

where i=m and m=3, 4, 5 or 6,
in combination with
   X=—OM when a=1,
   or
   X=[(CH₂)ₙSi(OM)R₂], [(CH₂)ₙSiR₃₋ₐ[(CH₂)ₙSi(OM)R₂]ₐ]
   and/or
   [(CH₂)ₙSiR₃₋ₐ[(CH₂) ₙSiR₃₋ₐ[(CH₂)ₙSi(OM)R₂]ₐ]ₐ]
   when a=1, 2 or 3, where
   M is a metalloid or metal which may optionally contain further substituents and M may be the same or different within the molecule.

2. Carbosilane dendrimers according to claim 1, characterised in that they are

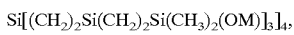

3. Carbosilane dendrimers according to claim 1, characterized in that each M is selected from the group consisting of B, Al, Ga, In, Ge, Sn, Pb, As, Sb, Bi, Ti, Zr, Hf, V, Nb, Ta, Cr, Mo, W, Re, Fe, Ru, Os, Rh, Ir, Pt, Cu, Ag and Au.

4. Carbosilane dendrimers according to claim 1, characterized in that each M is selected from the group consisting of Ti, Zr and Hf.

5. A method of preparing carbosilane dendrimers according to claim 1, characterized in that an SiOH-functional carbosilane of general formula

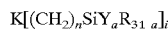

where n=2, 3, 4, 5 or 6, and R=C₁–C₁₈ alkyl or C₆–C₁₈ aryl, wherein n and R may be the same or different within the molecule, where
A) K=[R₄₋ᵢSi] when i=3 or 4 or

B) K =

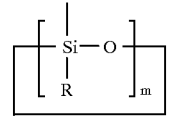

where i=m and m=3, 4, 5 or 6,
in combination with Y=(OH) when a=1, or
   Y=[(CH₂)ₙSi(OH)R₂], [(CH₂)ₙSiR₃₋ₐ[(CH₂)ₙSi(OH)R₂]ₐ]or
   [(CH₂)ₙSiR₃₋ₐ[(CH₂)ₙSiR₃₋ₐ[(CH₂)ₙSi(OH)R₂]ₐ]ₐ]
   when a=1, 2 or 3,
is reacted with at least one metal and/or metalloid compound, optionally in the presence of a base.

6. A method of preparing carbosilane dendrimers according to claim 5, characterised in that

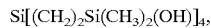

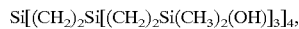

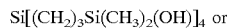

is used as the SiOH-functional carbosilane dendrimer.

7. A method of preparing carbosilane dendrimers according to claim 5, characterized in that the metal and/or metalloid compounds are substituted with at least one ligand Z, where Z is selected from the group consisting of Cl, Br, I and OR, where R=alkyl or aryl, and form Si—O—M bonds with the separation of HZ.

8. A method of preparing carbosilane dendrimers according to claim 5, characterized in that the base is one or more triorganoamines.

9. A method of using the carbosilane dendrimers according to claim 1, comprising the step of adding the carbosilane dendrimers to a reaction system as a homogeneous or heterogeneous catalyst.

10. A method of using the carbosilane dendrimers according to claim 1, comprising the step of adding the carbosilane dendrimers to a reaction system as an additive or constituent for the production or functionalization of inorganic-organic hybrid materials.

11. Carbosilane dendrimers according to claim 2, characterized in that each M is selected from the group consisting of B, Al, Ga, In, Ge, Sn, Pb, As, Sb, Bi, Ti, Zr, Hf, V, Nb, Ta, Cr, Mo, W, Re, Fe, Ru, Os, Rh, Ir, Pt, Cu, Ag and Au.

12. Carbosilane dendrimers according to claim 2, characterized in that each M is selected from the group consisting of Ti, Zr and Hf.

13. A method of preparing carbosilane dendrimers according to claim 6, characterized in that the metal and/or metalloid compounds are substituted with at least one ligand Z, where Z is selected from the group consisting of Cl, Br, I and OR, where R=alkyl or aryl, and form Si—O—M bonds with separation of HZ.

14. A method of preparing carbosilane dendrimers according to claim 6, characterized in that the base is one or more triorganoamines.

15. A method of preparing carbosilane dendrimers according to claim 7, characterized in that the base is one or more triorganoamines.

* * * * *